United States Patent [19]

Century

[11] Patent Number: 5,379,778
[45] Date of Patent: Jan. 10, 1995

[54] PLETHYSMOGRAPHIC APPARATUS

[76] Inventor: Theodore J. Century, 702 W. Carpenter La., Philadelphia, Pa. 19119

[21] Appl. No.: 84,425

[22] Filed: Jun. 29, 1993

[51] Int. Cl.$^6$ .............................................. A61G 10/00
[52] U.S. Cl. ...................................... 128/718; 600/21
[58] Field of Search ............... 128/671, 694, 716, 718, 128/719, 720, 721, 725, 747, 203.24, 204.25, 204.26; 600/21, 22; 49/68; 34/242

[56] References Cited

U.S. PATENT DOCUMENTS

| | | | |
|---|---|---|---|
| H145 | 10/1986 | James | 128/716 |
| 3,309,684 | 3/1967 | Kahn et al. | 600/21 |
| 3,877,427 | 4/1975 | Alexeeu et al. | 600/21 |
| 3,976,053 | 8/1976 | Reininghaus | 128/724 |
| 4,085,741 | 4/1978 | Rotgans . | |
| 4,402,315 | 9/1983 | Tsuda et al. | 128/716 |
| 4,622,852 | 11/1986 | James et al. . | |
| 4,841,982 | 6/1989 | Nikiforov et al. . | |

FOREIGN PATENT DOCUMENTS 9218084  10/1992  WIPO ............................... 600/21

OTHER PUBLICATIONS

Louis Diamond & Margaret O'Donnell, "Pulmontary mechanics in normal rats", J. Appl. Physiol.: Respirat. Environ. Exercise Physiol. 43(6): 942–948, 1977, USA.
Frantisek Palecek, "Measurement of ventilatory mechanics in the rat", J. Appl. Physiol. 27(1): 149–156, 1969, USA.

Primary Examiner—Lee S. Cohen
Assistant Examiner—Samuel Gilbert
Attorney, Agent, or Firm—Paul & Paul

[57] ABSTRACT

A plethysmographic device is disclosed which is adapted for receiving a laboratory animal for measuring pulmonary ventilation thereof. The plethysmographic device includes a containment member which defines a sealed environment and which includes as portions thereof at least a first and a second member and a seal. The first member is adapted to releasably engage the second member with the seal defining a self-supporting radial seal being provided therebetween for defining the sealed environment of the containment member. The containment member also includes an inlet and an outlet. The inlet of the containment member is in communication with a supply which is adapted to regulate the environment of the containment member. The outlet of the containment member is in communication with a response device which is adapted for monitoring the environment of the containment member. The first member includes as portions thereof a receptacle, a platform, and a base. The base is adapted to support the device in order that the first member will not collapse when released from engagement with the second member.

43 Claims, 2 Drawing Sheets

PLETHYSMOGRAPHIC APPARATUS

BACKGROUND OF THE INVENTION

1. Field of the Invention

The present invention relates generally to plethysmographic devices and more particularly to plethysmographic devices adapted for use with laboratory animals.

2. Background of the Invention

Generally, plethysmography relates to a process for measuring variations in volume of a particular organ, part, limb or body. Presently, there are a number of plethysmographic devices known in the art which are used for many specific purposes. One type are adapted for measuring various pulmonary parameters of animals during laboratory testing procedures. For example, the plethysmograph in such applications can be utilized to determine different aspects of pulmonary function, for example to measure lung volumes, residual volume of the lung, airway resistance, and pulmonary blood flow. In operation, volume and/or pressure changes are monitored over a particular time period for determining the respective pulmonary characteristics in accordance with Boyle's law ($PV=K$). Generally, plethysmographic devices of this type comprise sealed containers which are adapted to receive the body of the animal therein for testing. In particular, a removable section is included in the container which allows access to the interior of the device.

In addition, it is oftentimes desirable that the animal is anesthetized and tracheotomized prior to operation within the plethysmographic container. In this regard, a flat bed-like portion is utilized in order to support the animal within the container during operation. Further, numerous hook-up fittings can also be provided within the container in order to allow access to the animal after the device has been sealed. For example, in many instances it is desirable to provide a cardiovascular line or other monitoring apparatus in communication with the animal.

One problem with such prior art devices, however, occurs as a result of the seal of the device. Generally, the removable section of the plethysmographic container is connected by a seal to the rest of the container during operation. However, such seals are typically of the end-on or face-seal type, which require a cumbersome latching mechanism for joining the two parts of the container. Another problem occurs when the container is in the opened position in order to gain access To the animal contained therein. Specifically, an additional support is required in this position in order to stabilize the bed portion of the device. Still another problem is that it is oftentimes difficult to access the various small tubing ports which may be located in a recess in the container wall. Specifically, connecting the numerous small tubings, which are utilized for monitoring the animal, to these tubing ports, all within the space occupied by the head of the animal, can be a daunting task for the individual performing the testing procedure. Another problem occurs as a result of bodily excrement produced by the animal during the course of an experiment, when the container is in its sealed state. Specifically uncontained accumulation of such excrement, which may be excessive due to the substances to which the animal is subjected, makes cleaning of the experimental container a distasteful and difficult task.

The present invention has has been developed in view of the foregoing and to overcome the deficiencies of the prior art.

SUMMARY OF THE INVENTION

The present invention provides a plethysmographic device adapted for receiving a laboratory animal for measuring pulmonary ventilation thereof. The plethysmographic device of the present invention includes a containment means which defines a sealed environment and includes as portions thereof at least a first member and a second member. The first member is adapted to releasably engage a sealing means associated with the second member for defining the sealed environment of the containment means. The containment means further includes an inlet and an outlet. The inlet of the containment means is in communication with a supply means which is adapted for regulating the environment of the containment means. The outlet of the containment means is in communication with response means, which is adapted for monitoring the environment of the containment means.

An object of the present invention is to provide a plethysmographic device having an improved seal adapted to facilitate opening and closing thereof.

It is a further object of the present invention to provide a plethysmographic device capable of supporting a bed-like portion provided therein when the device is in its opened position.

It is still a further object of the present invention to provide a plethysmographic device which will facilitate hook-up of the animal contained therein pursuant to the carrying out of the test procedure.

It is another object of the present invention to provide a plethysmographic device which will contain bodily excrement produced by the animal and which will facilitate cleaning of the device.

It is still a further object of the present invention to provide a plethysmographic device which is durable in use and which is relatively simple to operate.

These and other objects of the present invention will become more readily apparent when taken into consideration with the following description and the attached drawings.

DETAILED DESCRIPTION OF THE PREFERRED EMBODIMENTS

Figure 1:
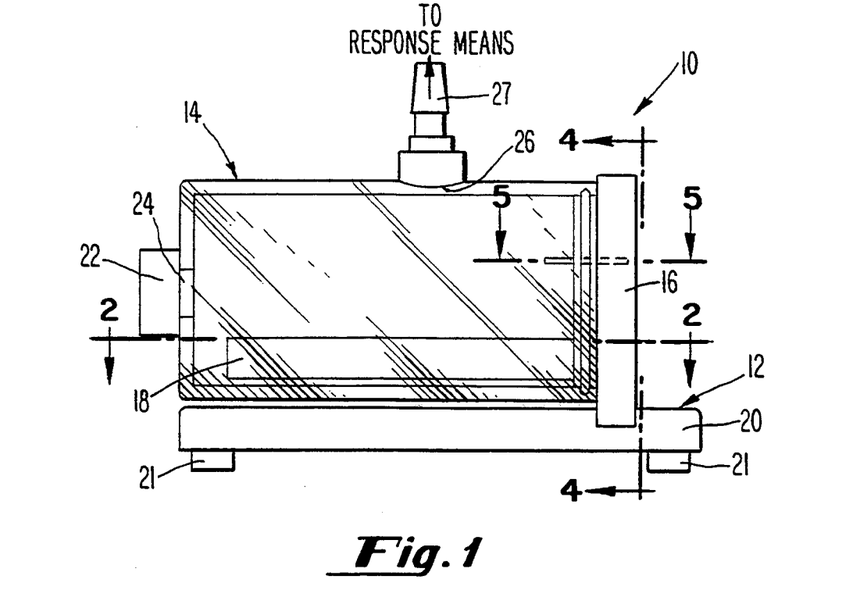
FIG. 1 is a front elevational view of a plethysmographic device according to the present invention.
Figure 2:
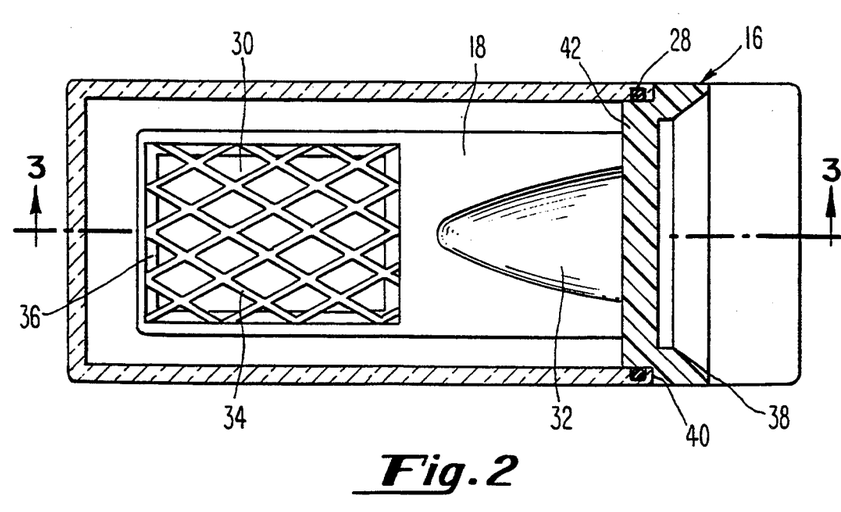
FIG. 2 is a sectional plan view of the plethysmographic device of FIG. 1 taken along the lines of 2—2.

Referring now to the drawings in detail wherein like reference numerals indicate like elements throughout the several views, there is shown in FIG. 1 a front elevational view of a plethysmographic device 10 according to the present invention. The plethysmographic device 10 as shown comprises a containment means which includes a first member 12 and a second member 14. The first member 12 includes as portions thereof a receptacle means 16, a platform 18 and a base member 20. The base, member 20 includes four legs 21, screwed or otherwise connected therein by conventional techniques (only two of which are visible), preferably comprised of rubber or other material, for supporting the base member 20. The second member 14 as shown includes an inlet 24 and an outlet 26, with the inlet 24 being in connection with a supply means 22, preferably comprising a pneumotach device, and the outlet 26 in connection with an outlet portion 27 which is in communication with a response means, preferably comprising a pressure transducer device. As best seen in FIGS. 1 and 2, the second member 14 is provided with a cavity therein which defines an inner surface and is in engagement with the first member 12. In this position, the receptacle means 16 of the first member 12 is in contact with a sealing means 28 provided within an aperture in the inner surface of the cavity of the second member 14. Preferably, the sealing means 28 comprises an O-ring or the like which is adapted to be received within the aperture formed within the second member 14.

Figure 3:
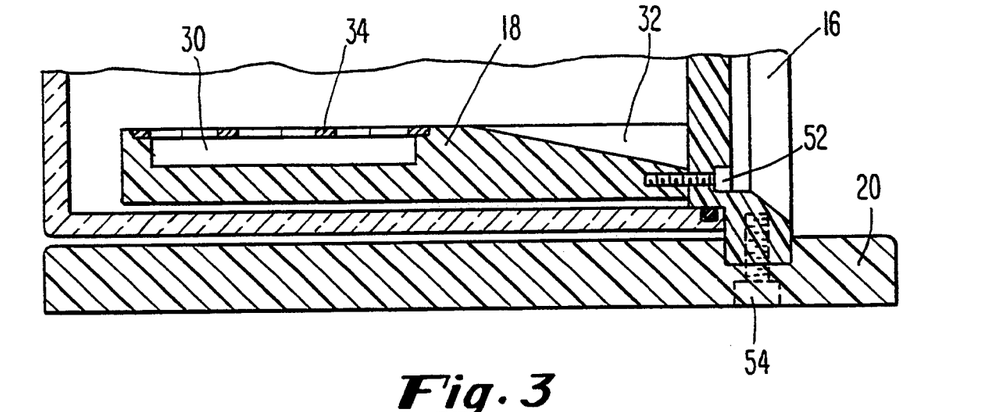
FIG. 3 is a sectional elevational view of the plethysmographic device of FIG. 2 taken along the line 3—3.

As best shown in FIGS. 2 and 3, the platform 18 of the first member 12 is provided extending outwardly from the receptacle means 16. The platform 18 as shown is included with a cavity 30 provided within its upper surface and also a tapered portion 32, which tapers inwardly proximate a center thereof, adjacent the cavity 30. A screen 34 as shown is also provided which is received within a downwardly stepped section 36 of the platform 18, covering the cavity 30.

Figure 4:
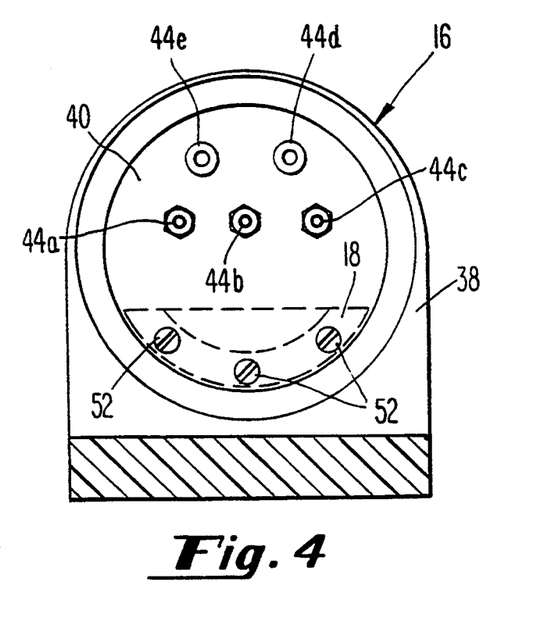
FIG. 4 is a right side elevational view of the plethysmographic device of FIG. 1 taken along the line 4—4.

As best illustrated in FIGS. 1 and 4, the receptacle means 16 includes as portions thereof a back end 38 having a substantially cone-shaped cavity extending therein, a front end 40 having a substantially annular cavity extending therein and a boss 42 extending outwardly from the front end 40. The receptacle means 16 further includes at least one fitting extending therethrough from the front end 40 through the boss 42, preferably the fittings 44a–44e are provided for a purpose described below.

In operation, a laboratory animal (not shown), such as a mouse, rat, guinea pig, etc., is placed on the platform 18 when the containment means is in its opened position with the first member 12 released from the second member 14. In this position, the receptacle means 6 and the platform 18 are supported by the base member 20. As indicated earlier, in most instances, the animal is anesthetized prior to being placed upon the platform 18. In such instances, the animal is placed on its back with its head extending backwardly into the tapered portion 32 and its lower extremities placed on the screen 34 above the cavity 30. After which, the first member 12 and second member 14 are engaged in the position shown in FIG. 2 with the boss 42 in engagement with the sealing means 28.

Figure 5:
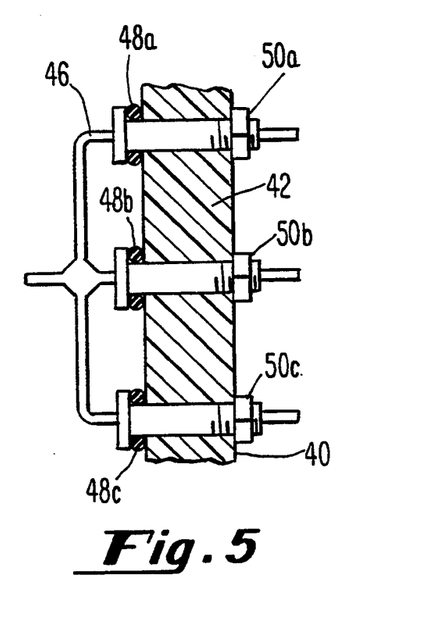
FIG. 5 is a sectional plan view of the plethysmographic device of FIG. 1 taken along the line 5—5 and showing a tracheal manifold mounted therein.

Further, as noted earlier, it is oftentimes desirable to also tracheotomize the animal. This procedure can be performed after the animal is placed on the platform 18 and before the first member 12 has been sealed in engagement with the second member 14. As shown in FIG. 5, a manifold means 46 is included which is adapted to be received through the fittings 44a–44c. O-rings 48a–48c are received adjacent the fittings 44a–44c in order to seal the connection with the manifold means 46. Threaded nuts 50a–50c are also included which are adapted to be received onto a threaded section of the manifold means 46 in order to retain the manifold means 46 within the fittings 44a–44c. A tracheal tube (not shown) or other device can be applied to the animal via the manifold means 46. Access to the animal can also be made through the fittings 44d–44e, for example, an intravascular line or other monitoring device can extend through the fittings 44d–44e and in connection with the animal. 0-ring fittings (not shown), similar to the O-rings 48a–48c, can also be received within the fittings 44d–44e for providing a sealed passage.

Furthermore, following the required preparations of the animal, the first member 12 and second member 14 are connected in the arrangement shown in FIG. 1. The supply means 22 operates as a moderately high-resistance pathway for ambient air flow into and out of the sealed containment means. Used in conjunction with the response means 26, air flow into and out of the container can be measured, and influences of the animal contained therein determined.

As best seen in FIGS. 3 and 4, the receptacle means 16 is in connection with the platform 18 via screws 52. Similarly, the base member 20 is connected to the receptacle means 16 via two screws 54 (only one of which is visible in FIG. 3). It should be noted, however, that any suitable connector can be utilized for attaching the aforementioned structures, or in some circumstances, the elements can be formed as one integral unit. Preferably, the first and second members 12 and 14 of the plethysmographic device 10 are manufactured by conventional techniques from thermoplastic or thermosetting materials, such as polymethyl methacrylate, however other suitable materials, which will provide a rigid structure, can also be utilized.

The plethysmographic device of the present invention possesses several advantages over conventional plethysmographic devices. A particular advantage of the present invention is that: the arrangement of the device provides a precision, pre-loaded sliding radial seal which provides its own mechanical support. In prior art devices, the sealing of the two parts of the container is effected by means of an imprecise, end-on or face type seal, which requires additional cumbersome mechanical connections to maintain the integrity of the seal. Rather, the present invention facilitates a smooth, self-supporting connection and disconnection of the first member 14 and the second member 16 of the device. As best seen in FIG. 2, the boss 42 of the receptacle means 16 is slidably engagable via its outside surfaces with the sealing means 28 provided between the first member 12 and the second member 14.

Another advantage of the plethysmographic device of the present invention is that the platform 18, which operates as a bed for supporting the animal during operation, is in connection with the base member 20. As best illustrated in FIG. 1, the base member 20 will support the platform 18 both when the first and second members 12 and 14 are connected in the arrangement of FIG. 1, or when the first member 12 and second member 14 are disconnected from one another. In prior art devices, it is required to provide an additional support for holding the bed of the device when the device is in an opened position.

Furthermore, another advantage of the present plethysmographic device over conventional plethysmographic devices is that a smaller, more compact and less cumbersome device is provided. Specifically, the manifold means 46 allows access through the device directly to the laboratory animal without also requiring an arrangement of individual tubings or structures which can be rather cumbersome during operation. Furthermore, another advantage is that the manifold means 46 results in a structure which requires a shorter length of tubing for connection to the animal than prior art devices, thus minimizing dead space. Further, another advantage is that the integral manifold means 46 also works to eliminate the necessity of having a number of fittings as with prior art devices. In the present invention, the novel manifold means 46, which incorporates a structure having three in and one out passages, allows access therethrough with a number of different devices.

It is still another advantage of the present plethysmographic device in that unlike conventional plethysmographic devices, the present device can be quickly and conveniently cleaned after use. In conventional devices, bodily excrement produced from the animal contaminates all the lower surfaces as well as the seal of the sealed container during operation, thus making cleaning of the container a formidable task. As best seen in FIGS. 2 and 3 of the present invention, the cavity 30 is adapted to receive and retain bodily excrement produced from the animal so as to not contaminate the container during operation, and to facilitate cleaning after operation.

Compared to prior art design, the present plethysmographic device also facilitates the process of effective cleaning due to the design of the manifold means 46, which can be easily removed from the receptacle means 16 via the threaded nuts 50a–50c. Upon removal of the manifold means 46, this portion can be cleaned and thereafter be reinstalled within the receptacle means 16 for operation of the device.

In addition, the present invention provides another advantage in that it will allow for easier and quicker preparation of the animal prior to testing. In conventional plethysmographic devices, it can be rather cumbersome for application of a tracheal tube or similar to the animal prior to operation. As best shown in FIGS. 2 and 3 of the present invention, upon receipt of the animal in the device, the animals head will lie within the tapered portion 32 of the device, thus tilting backwardly exposing the neck region. As such, this arrangement will facilitate the application of the tracheal connection via the manifold means 46.

It will be recognized by those skilled in the art that changes may be made by the above-described embodiments of the invention without departing from the broad inventive concepts thereof. For example, the sealing means 28, which is described provided within an aperture in the inner surface of the second member 14 for engaging tile boss 42 of the first member 12, can also be provided within the first member 12, in particular surrounding the boss 42 and within an aperture therein, for slidably engaging the inner surface of the cavity of the second member 14. In addition, in some instances, the present plethysmographic device can also have application with larger sized animals such as humans. Additionally, the second member 16, which in the present embodiment is a cylindrical member, can also be formed having any suitable configuration for the same purpose. Furthermore, the first member 14, which comprises the substantially annular receptacle means 16 having, as portions, the substantially annular first section extending from the backend 38 to the front end 40, and the substantially annular boss 42 extending outwardly from the front end 40, can be comprised of any suitable configuration which will allow engagement of the first and second members 14 and 16. In addition, where in the present embodiment an inlet and outlet are shown in connection with a supply means and a response means, respectively, it should be understood that additional ports can also be provided in connection with other types of devices without departing from the spirit of the invention. It is understood, therefore, that this invention is not limited to the particular embodiments disclosed, but it is intended to cover all modifications which are within the scope and spirit of the invention as defined by the appended claims.

I claim:

1. A plethysmographic device adapted for receiving a laboratory animal for measuring pulmonary ventilation thereof, the plethysmographic device comprising:

a containment member defining a sealed environment and including as portions thereof at least first and second members and a sealing means comprising a self-supporting radial seal for providing the sealed environment of the containment member, wherein the first member is adapted to releasably engage the second member and the sealing means is provided between the first member and the second member when engaged for providing the self-supporting radial seal defining the sealed environment of the containment member, wherein the second member includes therein a cavity defining an inner surface and the first member includes a receptacle having a back end, a front end and a boss, the front end of the receptacle being generally parallel the back end and the boss defining an outer surface extending generally perpendicularly from the front end of the receptacle, wherein the outer surface of the boss is adapted to slidably engage the inner surface of the second member upon engagement thereof, with the inner surface of the second member being substantially parallel the outer surface of the boss and the sealing means being provided therebetween for providing the self-supporting radial seal defining the sealed environment of the containment member, the laboratory animal being receivable within the containment member for measuring the pulmonary ventilation thereof, wherein the containment member further includes an inlet and an outlet, supply means for regulating the environment of the containment member in communication with the inlet of the containment member and response means for monitoring the environment of the containment member in communication with the outlet of the containment member whereby the supply means and response means are adapted for measuring the pulmonary ventilation of the laboratory animal.

2. A plethysmographic device according to claim 1, wherein the sealing means is disposed within an aperture formed in the inner surface of the second member and is slidably engagable with the intersurface of the boss of the first member upon engagement therewith.

3. A plethysmographic device according to claim 1, wherein the sealing means is disposed within an aperture formed in the outer surface of the boss of the first member and is slidably engagable with the inner surface of the second member upon engagement therewith.

4. A plethysmographic device according to claim 1, wherein the first member further includes a platform in connection with the boss of the receptacle and projecting outwardly therefrom and within the containment member adapted for receiving and supporting the animal thereon.

5. A plethysograpic device according to claim 4, wherein the platform includes an upper and a lower surface, with the upper surface having therein an aperture defining a cavity adapted for receiving and retaining bodily excrement produced by the animal, and wherein the platform is tapered inwardly proximate a center thereof from the upper surface toward the lower surface and in a direction of the receptacle adapted for receiving a head of the animal, whereby the animal's head is angled backwardly for facilitating application of a tracheal tube.

6. A plethysmographic device according to claim 4, wherein the first member further includes a base member in connection with the receptacle and adapted for supporting both the receptacle and the platform when released from the second member, and supporting the second member as well as the receptacle and the platform when the first member is in engagement with the second member.

7. A plethysmographic device according to claim 1, further comprising monitoring means for measuring a response of the laboratory animal in communication with the receptacle.

8. A plethysmographic device according to claim 7, wherein the monitoring means includes a manifold member adapted for being removably receivable within the receptacle in connection with a tracheal tube in communication with the laboratory animal.

9. A plethysmographic device according to claim 8, wherein the receptacle includes at least one sealed fitting extending therethrough adapted for retaining the manifold member, wherein the manifold member extends through the sealed fitting of the receptacle and includes a first end and a second end therein, with the first end being proximate the back end of the receptacle and the second end being proximate the boss of receptacle when received thereon.

10. A plethysmographic device according to claim 7, wherein the receptacle includes at least one sealed fitting therein adapted for receiving an intravascular line in communication with the laboratory animal.

11. A plethysmographic device adapted for receiving a laboratory animal for measuring pulmonary ventilation thereof, the plethysmographic device comprising:
a containment member defining a sealed environment and including as portions thereof at least a first member in association with a second member, with the first member being adapted to releasably engage the second member for defining the sealed environment of the containment member, the laboratory animal being receivable within the containment member for measuring the pulmonary ventilation thereof, wherein the containment member further includes an inlet and an outlet, supply means for regulating the environment of the containment member in communication with the inlet of the containment member and response means for monitoring the environment of the containment member in communication with the outlet of the containment member, whereby the supply means and response means are adapted for monitoring the pulmonary ventilation of the laboratory animal, the first member further including a base member supporting the first member when the first member is released from engagement with the second member, and supporting the second member as well as the first member when the first member is sealed in engagement with the second member, wherein the first member further includes a generally elongate receptacle for releasably engaging the second member, with the base member being adapted for supporting the receptacle in a first orientation when the first member is in engagement with the second member and a second orientation when the first member is released from engagement with the second member, wherein the first orientation of the receptacle corresponds substantially to the second orientation of the receptacle, wherein the first member further includes a platform in connection with the receptacle and projecting outwardly therefrom adapted for supporting the animal thereon, wherein the platform comprises a generally elongate member, with the base member being adapted for supporting the platform in a first orientation when the first member is in engagement with the second member and a second orientation when the first member is released from engagement with the second member, wherein the first orientation of the platform corresponds substantially to the second orientation of the platform.

12. A plethysmographic device according to claim 11, wherein the second member includes therein a cavity defining an inner surface and the receptacle includes a back end, a front end and a boss, with the boss extending outwardly from the front end and adapted to slidably engage the inner surface of the second member with a sealing means for providing the sealed environment of the containment member therebetween upon engagement thereof, wherein the sealing means provides a self-supporting sealed environment, the base member further comprising a generally elongate member in connection with the receptacle and projecting outwardly therefrom, wherein the platform is substantially parallel the base member when the first member is both in engagement with and released from engagement with the second member.

13. A plethysmographic device according to claim 11, wherein the platform includes an upper and a lower surface, with the upper surface having therein an aperture defining a cavity adapted for receiving and retaining bodily excrement produced by the animal, and wherein the platform is tapered inwardly proximate a center thereof from the upper surface toward the lower surface and in a direction of the receptacle adapted for receiving a head of the animal, whereby the animal's head is angled backwardly for facilitating application of a tracheal tube.

14. A plethysmographic device according to claim 11, further comprising monitoring means for measuring a response of the laboratory animal in communication with the receptacle.

15. A plethysmographic device according to claim 14, wherein the monitoring means includes a manifold member adapted for being removably receivable within the receptacle in connection with a tracheal tube in communication with the laboratory animal.

16. A plethysmographic device according to claim 15, wherein the receptacle includes at least one sealed fitting extending therethrough adapted for retaining the manifold member, wherein the manifold member extends through the sealed fitting of the receptacle and includes a first end and a second end therein, wherein the receptacle includes a back end and a boss, with the first end of the manifold member being proximate the back end of the receptacle and the second end of the manifold member being proximate the boss of the receptacle when received therein.

17. A plethysmographic device according to claim 14, wherein the receptacle includes at least one sealed fitting therein adapted for receiving an intravascular line in communication with the laboratory animal.

18. A plethysmographic device adapted for receiving a laboratory animal for measuring pulmonary ventilation thereof, the plethysmographic device comprising:
a containment member defining a sealed environment and including as portions thereof at least a first member in association with a second member, with the first member being adapted to releasably engage the second member for defining the sealed environment of the containment member, the laboratory animal being receivable within the containment member for measuring pulmonary ventilation thereof, wherein the containment member further includes an inlet and an outlet, supply means for regulating the environment of the containment member in communication with the inlet of the containment member and response means for monitoring the environment of the containment member, in communication with the outlet of the containment member, whereby the supply means and the response means are adapted for measuring the pulmonary ventilation of the laboratory animal, monitoring means for measuring a response of the laboratory animal in communication with the first member, wherein the monitoring means includes a manifold member removably receivable within the first member for connection with a tracheal tube in communication with the laboratory animal, whereby the manifold member is adapted to extend through the first member when received therein, wherein the first member includes a receptacle with the receptacle including a back end, a front end and a boss, with the boss extending outwardly from the front end adapted for engaging the second member in a closed position of the containment member, the receptacle further includes at least one sealed fitting extending therethrough for retaining the manifold member, wherein the manifold member extends through the sealed fitting of the receptacle and includes a first end and a second end therein, with the first end being proximate the back end of the receptacle and the second end being proximate the boss of receptacle when received therein.

19. A plethysmographic device according to claim 18, wherein the receptacle includes at least a second sealed fitting adapted for receiving an intravascular line in communication with the laboratory animal.

20. A plethysmographic device according to claim 19, wherein the receptacle includes at least five sealed fittings, with three fittings receiving the manifold member and the remaining two adapted for fittings receiving an intravascular line.

21. A plethysmographic device according to claim 19, wherein the second member includes therein a cavity defining an inner surface adapted for slidably engaging the boss of the receptacle with a sealing means positioned therebetween upon engagement thereof, wherein the sealing means provides a self-supporting sealed environment.

22. A plethysmographic device according to claim 19, wherein the first member further includes a platform in connection with the boss of the receptacle projecting outwardly therefrom and adapted for receiving and supporting the animal thereon.

23. A plethysmographic device according to claim 22, wherein the platform includes an upper and a lower surface, with the upper surface having therein an aperture defining a cavity adapted for receiving and retaining bodily excrement produced by the animal, and wherein the platform is tapered inwardly proximate a center thereof from the upper surface toward the lower surface and in a direction of the receptacle adapted for receiving a head of the animal, whereby the animal's head is angled backwardly for facilitating application of a tracheal tube.

24. A plethysmographic device according to claim 22, wherein the first member further includes a base member adapted for supporting both the receptacle and the platform when released from the second member, and supporting the second member as well as the receptacle and the platform when the first member is in engagement with the second member.

25. A plethysmographic device adapted for receiving a laboratory animal for measuring pulmonary ventilation thereof, the plethysmographic device comprising:
a containment member defining a sealed environment and including as portions thereof at least a first member in association with a second member, with the first member being adapted to releasably engage the second member for defining the sealed environment of the containment member, the laboratory animal being receivable within the containment member for measuring the pulmonary ventilation thereof, wherein the containment member further includes an inlet and an outlet, supply means for regulating the environment of the containment member in communication with the inlet of the containment member and response means for monitoring the environment of the containment member in communication with the outlet of the containment member, response means whereby the supply means and the response means are adapted for measuring the pulmonary ventilation of the laboratory animal, the first member further including a receptacle adapted for releasably engaging the second member and a platform, the platform being in connection with the receptacle and projecting outwardly therefrom adapted for receiving and supporting the animal thereon, the platform including an upper and a lower surface, with the upper surface having therein an aperture defining a platform cavity adapted for receiving and retaining bodily excrement produced by the animal.

26. A plethysmographic device according to claim 25, wherein the platform is tapered inwardly proximate a center thereof from the upper surface toward the lower surface and in a direction of the receptacle for receiving a head of the animal, whereby the animal's head is angled backwardly for facilitating application of a tracheal tube.

27. A plethysmographic device according to claim 26, wherein the second member includes therein a second member cavity defining an inner surface and the receptacle includes a back end, a front end and a boss, with the boss extending outwardly from the front end and adapted to slidably engage the inner surface of the second member with a sealing means for providing the sealed environment of the containment member therebetween upon engagement thereof, wherein the sealing means provides a self-supporting sealed environment.

28. A plethysmographic device according to claim 26, wherein the first member further includes a base member supporting both the receptacle and the platform when released from the second member, and supporting the second member as well as the receptacle and the platform when the first member is in engagement with the second member.

29. A plethysmographic device according to claim 26, monitoring means for measuring a response of the laboratory animal in communication with the receptacle.

30. A plethysmographic device according to claim 29, wherein the monitoring means includes a manifold member adapted for being removably receivable within the receptacle in connection with a tracheal tube in communication with the laboratory animal.

31. A plethysmographic device according to claim 30, wherein the receptacle includes at least one sealed fitting extending therethrough adapted for retaining the manifold member, wherein the manifold member extends through the sealed fitting of the receptacle and includes a first end and a second end therein, with the first end being proximate the back end of the receptacle and the second end being proximate the boss of receptacle when received therein.

32. A plethysmographic device according to claim 29, wherein the receptacle includes at least a second sealed fitting adapted for receiving an intravascular line in communication with the laboratory animal.

33. A plethysmographic device adapted for receiving a laboratory animal for measuring pulmonary ventilation thereof, the plethysmographic device comprising:
a containment member defining a sealed environment and including as portions thereof at least a first member in association with a second member, with the first member being adapted to releasably engage the second member for defining the sealed environment of the containment member, the laboratory animal being receivable within the containment member for measuring the pulmonary ventilation thereof, wherein the containment member further includes an inlet and an outlet, supply means for regulating the environment of the containment member in communication with the inlet of the containment member and response means for monitoring the environment of the containment member in communication with the outlet of the containment, whereby the supply means and the response means are adapted for measuring the pulmonary ventilation of the laboratory animal, the first member further including a receptacle adapted for releasably engaging the second member and a platform, the platform being in connection with the receptacle and projecting outwardly therefrom adapted for receiving and supporting the animal thereon, wherein the platform includes an upper and a lower surface and is tapered inwardly proximate a center thereof from the upper surface toward the lower surface and in a direction of the receptacle for receiving a head of the animal, whereby the animal's head is angled backwardly for facilitating application of a tracheal tube, wherein the upper surface of the platform further includes therein an aperture defining a cavity adapted for receiving and retaining bodily excrement produced by the animal.

34. A plethysmographic device according to claim 33, wherein the platform comprises a generally elongated member having a first end in connection with the receptacle, a second end and a generally elongated section connecting the first and second ends thereof, the generally elongated section being confined within the second member when the receptacle is in engagement with the second member.

35. A plethysmographic device according to claim 34, wherein the first member further includes a base member adapted for supporting both the receptacle and the platform when released from the second member, and supporting the second member as well as the receptacle and the platform when the first member is in engagement with the second member.

36. A plethysmographic device according to claim 34, further comprising monitoring means for measuring a response of the laboratory animal in communication with the receptacle.

37. A plethysmographic device according to claim 36, wherein the monitoring means includes a manifold member adapted for being removably receivable within the receptacle in connection with a tracheal tube in communication with the laboratory animal.

38. A plethysmographic device according to claim 37, wherein the receptacle includes at least one sealed fitting extending therethrough adapted for retaining the manifold member, wherein the manifold member extends through the sealed fitting of the receptacle and includes a first end and a second end therein, with the first end being proximate the back end of the receptacle and the second end being proximate the boss of receptacle when received therein.

39. A plethysmographic device according to claim 36, wherein the receptacle includes at least a second sealed fitting adapted for receiving an intravascular line in communication with the laboratory animal.

40. A plethysmographic device according to claim 34, wherein the second member includes therein a cavity defining an inner surface and the receptacle includes a back end, a front end and a boss, with the boss extending outwardly from the front end and adapted to slidably engage the inner surface of the second member with a sealing means for providing the sealed environment of the containment member therebetween upon engagement thereof, wherein the sealing means provides a self-supporting sealed environment, wherein the first end of the platform is in connection with and projecting outwardly from the boss of the receptacle, and the generally elongated section of the platform is confined within the cavity of the second member when the second member is in engagement with the receptacle.

41. A plethysmographic device adapted for receiving a laboratory animal for measuring pulmonary ventilation thereof, the plethysmographic device comprising:
a containment member defining a sealed environment and including as portions thereof at least first and second members and a sealing means for providing the sealed environment of the containment member, with the first member being adapted to releasably engage the second member and the sealing means being provided between the first and second members when engaged for defining the sealed environment of the containment member, the laboratory animal being receivable within the containment member for measuring the pulmonary ventilation thereof, wherein the second member includes therein a cavity defining an inner surface adapted for releasably receiving the first member, wherein the first member includes a receptacle having a back end, a front end and a boss, with the boss extending outwardly from the front end adapted for slidably engaging the inner surface of the second member with the sealing means therebetween upon engagement thereof, wherein the sealing means provides a self-supporting sealed environment, the containment member further including an inlet and an outlet, supply means for regulating the sealed environment of the containment member in communication with the inlet of the containment member and the response means for monitoring the sealed environment of the containment member in communication with the outlet of the containment member, whereby the supply means and response means are adapted for measuring the pulmonary ventilation of the laboratory animal, the first member including a platform in connection with the boss of the receptacle and projecting outwardly therefrom and within the containment member adapted for receiving and supporting the animal thereon, wherein the platform includes an upper and a lower surface, with the upper surface having therein an aperture defining a cavity adapted for receiving and retaining bodily excrement produced by the animal, and wherein the platform is tapered inwardly proximate a center thereof from the upper surface toward the lower surface and in a direction of the receptacle adapted for receiving a head of the animal, whereby the animal's head is angled backwardly for facilitating application of a tracheal tube, wherein the first member further including a base member supporting both the receptacle and the platform when released from the second member, and supporting the second member as well as the receptacle and the platform when the first member is in engagement with the second member, monitoring means for measuring a response of the laboratory animal in communication with the receptacle, wherein the monitoring means including a manifold member adapted for being removably receivable within the receptacle in connection with the tracheal tube in communication with the laboratory animal, wherein the receptacle includes at least one sealed fitting extending therethrough adapted for retaining the manifold member, wherein the manifold member extends through the sealed fitting of the receptacle and includes a first end and a second end therein, with the first end being proximate the back end of the receptacle and the second end being proximate the boss of receptacle when received therein, wherein the receptacle further includes at least a second sealed fitting adapted for receiving an intravascular line in communication with the laboratory animal.

42. A plethysmographic device according to claim 41, wherein the sealing means is disposed within a channel formed in the inner surface of the second member and is slidably engagable with the boss of the first member upon engagement therewith.

43. A plethysmographic device according to claim 41, wherein the sealing means is disposed within a channel formed in the boss of the first member and is slidably engagable with the inner surface of the second member upon engagement therewith.

* * * * *

UNITED STATES PATENT AND TRADEMARK OFFICE
CERTIFICATE OF CORRECTION

PATENT NO. : 5,379,778
DATED : January 10, 1995
INVENTOR(S) : Theodore J. Century It is certified that error appears in the above-indentified patent and that said Letters Patent is hereby corrected as shown below:

```
Column 3, line 46 after "receptacle means" and before
"and the platform" -- 6 -- should be -- 16 --.
```

Signed and Sealed this

Eighteenth Day of April, 1995

Attest:

BRUCE LEHMAN

*Commissioner of Patents and Trademarks*

*Attesting Officer*